(12) United States Patent
Chou (10) Patent No.: US 6,477,393 B1
(45) Date of Patent: Nov. 5, 2002

(54) NON-INVASIVE BLOOD GLUCOSE MEASUREMENT TECHNIQUES

(75) Inventor: Mau-Song Chou, Rancho Palos Verdes, CA (US)

(73) Assignee: TRW Inc., Redondo Beach, CA (US)

( * ) Notice: Subject to any disclaimer, the term of this patent is extended or adjusted under 35 U.S.C. 154(b) by 22 days.

(21) Appl. No.: 09/619,588

(22) Filed: Jul. 19, 2000

(51) Int. Cl.[7] .............................................. A61B 5/00
(52) U.S. Cl. ...................... 600/316; 600/322; 600/365
(58) Field of Search ............................... 600/309–310, 600/316, 319, 322, 326, 365; 356/39–42

(56) References Cited

U.S. PATENT DOCUMENTS

| | | | |
|---|---|---|---|
| 5,551,422 A | | 9/1996 | Simonsen et al. |
| 5,676,143 A | * | 10/1997 | Simonsen et al. ............ 600/316 |
| 5,774,223 A | * | 6/1998 | Urakami et al. ............. 356/394 |
| 5,782,755 A | | 7/1998 | Chance et al. |
| 5,882,301 A | * | 3/1999 | Yoshida ...................... 600/318 |
| 5,941,821 A | | 8/1999 | Chou |
| 5,945,592 A | | 8/1999 | Chou |
| 6,070,093 A | * | 5/2000 | Oosta et al. ................ 600/316 |
| 6,305,804 B1 | * | 10/2001 | Rice et al. ................... 351/221 |

OTHER PUBLICATIONS

O.S. Khalil, "Spectroscopic and clinical aspects of noninvasive glucose measurements," Clin. Chem. 45, 165 (1999).
L. Heinemann and G. Schmelzeisen–Redeker, "Noninvasive continuous glucose monitoring in type I diabetic patients with optical glucose sensors," Diabetologia 41, 848 (1998).
J.T. Bruulsema, M. Essenpreis, L. Heinemann, J.E. Hayward, M. Berger, F.A. Greis, T. Koschinsky, J. Sandahl–Christiansen, H. Orskov, T.J. Farrell, M.S. Patterson, and D. Bocker, "Detection of changes in blood glucose concentration in vivo with spatially resolved diffuse reflectance," OSA TOPS on Biomedical Optaical Spectroscopy and Diagnostics, vol. 3, 2 (1996).
J.T Bruulsema, J.E. Hayward, M., T.J. Farrell, M.S. Patterson, L. Heinemman, M. Berger, T. Koschinsky, J. Sandahl–Christiansen, H. Orskov, M. Essenpreis, G. Schmelzeisen–Redeker, and D. Bocker "Correlation between blood glucose concentration in diabetics and non-invasiveley measured tissue optical scattering coefficient," Opt. Lett., 22, 190 (1997).
J.S. Maier, S.A. Walker, S. Fantini, M.A. Franceschini, and E. Gratton, "Possible correlation between blood glucose concentration and the reduced scattering coefficient of tissues in the near infrared," Opt. Lett., 19, 2062 (1964).

(List continued on next page.)

Primary Examiner—Max Hindenburg
Assistant Examiner—Matthew Kremer
(74) Attorney, Agent, or Firm—McAndrews, Held & Malloy, Ltd.

(57) ABSTRACT

Non-invasive measurement of blood glucose is achieved by transmitting a ring of electromagnetic radiation to the surface of a subject (S) by a ring illuminator (22). The radiation diffuses into the subject illuminated and emits a portion of the radiation in area (E2) displaced from the illuminated area. A CCD camera (40) collects at least a portion of the emitted radiation and generates detection signals which are processed by a processor (100) in order to measure blood glucose concentration. The processing may be synchronized with the heart beat of the subject by an electrocardiogram (74).

21 Claims, 6 Drawing Sheets

OTHER PUBLICATIONS

M. Kohl, M. Essenpreis and M. Cope, "The influence of glucose concentration upon the transport of light in tissue–simulating phantoms," Phys. Med. Biol. 40, 1267 (1995).

T. J. Farrell, M.S. Patterson and B. Wilson, "A diffusion theory model of spatially resolved, steady–state diffuse reflectance for the noninvasive determination of tissue optical properties in vivo," Med. Phys. 19, 879 (1992).

T.J. Farrell, B.C. Wilson and M.S. Patterson, "The use of a neural network to determine tissue optical properties from spatially resolved diffuse reflectance measurements" Phy. Med. Biol. 37 2281 (1992).

T.J. Farrell, M.S. Patterson, J.E. Hayward, B.C. Wilson and E.R. Beck, "A CCD and neural network based instrument for the noninvasive determination of tissue optical properties in vivo." SPIE vol. 21335, 117 (1994).

S. J. Matcher, M. Cope and D.T. Deply, "In vivo measurements of the wavelength dependence of tissue–scattering coefficients between 760 and 900 nm measured with time–resolved spectroscopy," Appl. Opt. 36, 386 (1997).

A. Kienle, L. Lilge, M.S. Patterson, R.H. Hibst, R. Steiner, and B.C. Wilson, "Spatially resolved absolute diffuse reflectance measurements for noninvasive determination of the optical scattering and absorption coefficients of biological tissue", Appl. Opt. 35, 2304 (1996).

J.B. Fishkin, P.T.C. So., A.E. Cerussi, S. Fantini, M.A. Franceshini, and E. Gratton, "Frequency–domain method for measuring spectral properties in multiple–scattering media: methemoglobin absorption spectrum in a tissuelike phantom," Appl. Opt. 34, 1143 (1995).

World Health Organization, "Diabetes mellitus," WHO's Study Group Report Series 727, 1985.

National Diabetes Data Group, "Classification and diagnosis of diabetes mellitus and other categories of glucose intolerance," Diabetes, 27, 1039 (1979).

* cited by examiner

NON-INVASIVE BLOOD GLUCOSE MEASUREMENT TECHNIQUES

BACKGROUND OF THE INVENTION

This invention relates to non-invasive measurement of glucose in a biological matrix and more particularly relates to such measurements employing visible or near infrared radiation.

Many diabetic patients rely on self-monitoring of blood glucose for the proper regulation of an insulin therapy. Diabetic patients would benefit from a device capable of providing continuous non-invasive monitoring of their blood glucose levels. In addition to eliminating pain or possible infection, such monitoring can provide complete information on the blood glucose changes occurring over a long period of time. This information would enable the patient to optimize insulin doses and improve metabolic control.

Current progress on development of non-invasive glucose monitors has been recently reviewed in an article entitled "Spectroscopic and Clinical Aspects of Noninvasive Glucose Measurements," by O. S. Khalil, published in volume 45 of Clinical Chemistry, P. 165 (1999). According to Khalil, several research groups are trying to develop non-invasive glucose monitoring systems based on absorption measurements in the near infrared region, although none has been converted into a reliable glucose monitoring system. One of the main problems preventing such development is that the expected glucose absorption is very low as compared to other components in the tissue, such as water.

Previous known researchers have used a point illumination in conjunction with a spatially resolved diffuse reflectance technique. Using a point illumination, Heinemann and his coworkers have reported good correlation between the measured scattering coefficients and the blood glucose levels in thirty out of forty-one patients in their in vivo studies. These studies are reported in the following publications:

L. Heinemann and G. Schmelzeisen-Redeker, "Noninvasive continuous glucose monitoring in type I diabetic patients with optical glucose sensors," Diabetologia 41, 848 (1998).

J. T. Bruulsema, M. Essenpreis, L. Heinemann, J. E. Hayward, M. Berger, F. A. Greis, T. Koschinsky, J. Sandahl-Christiansen, H. Orskov, T. J. Farrell, M. S. Patterson, and D. Bocker, "Detection of changes in blood glucose concentration in vivo with spatially resolved diffuse reflectance," OSA TOPS on Biomedical Optical Spectroscopy and Diagnostics, Vol. 3, 2 (1996);

J. T. Bruulsema, J. E. Hayward, M., T. J. Farrell, M. S. Patterson, L. Heinemman, M. Berger, T. Koschinsky, J. Sandahl-Christiansen, H. Orskov, M. Essenspris, G. Schmelzeisen-Redeker, and D. Bocker "Correlation between blood glucose concentration in diabetics and noninvasively measured tissue optical scattering coefficient," Opt. Lett., 22, 190 (1997).

However, the approach of Heinemann et al. presents difficulties, such as the lack of sufficient sensitivity to resolve small changes in glucose level. In addition, the measurements were found to vary with locations and to drift with time. Local variation may be caused by heterogeneous distribution of light absorbing and light scattering structures in the tissue, whereas the time variation may be caused in part by changes in blood supply associated with heartbeats.

U.S. Pat. No. 5,551,422 (Simonsen et al., issued Sep. 3, 1996) discloses a method of spatially resolved reflectance for measurements of glucose and tissue by use of a point illumination. A line illumination arrangement was mentioned. However, the patent states that when the input irradiation site is in the form of a straight line, spatial resolution is lower, and the detection sensitivity becomes poor as compared to a point illumination. As a result, Simonson et al. discourage the use of a line illumination.

U.S. Pat. No. 5,782,755 (Chance et al., issued Jul. 21, 1998) discloses another variation of spatial resolved diffused reflectance for measurement of glucose in a biological system. Chance et al. use multiple spot light sources, such as flash bulbs, and a single detector. The light sources are spaced different distances along a single line from a detector and are sequenced at different time intervals to derive the spatial reflectance profiles.

BRIEF SUMMARY OF THE INVENTION

The preferred embodiment is useful for non-invasive measurement of blood glucose of a subject. In such an environment, glucose in a tissue can be measured by illuminating with electromagnetic radiation a first portion of the surface of the subject comprising a geometric element defined by moving a point in a path. The illuminated first portion results in a part of the radiation being emitted from the surface in a second portion displaced from the first portion. The radiation emitted from at least part of the second portion is detected within a field of view to generate detection signals. A processor analyzes the detection signals to measure the blood glucose of the subject.

The foregoing techniques offer a number of advantages. Detection sensitivity can be improved substantially as compared to a point illumination. The foregoing techniques allow averaging of scattering events over a large area of tissue. Such averaging reduces any inhomogeneity of the scattering structure in the tissue and thus improves reproducibility and reliability of the measurements. In addition, the foregoing techniques permit measurements of radiation reflectance at a distance farther away from the illumination site than prior techniques. Since the effective average light penetration is expected to be deeper into the skin at a far distance, it permits interaction of the photon in depth where the glucose is expected to be more abundant. The interaction with a rich glucose region can further result in improved detection sensitivity compared to a point illumination. In addition, it is possible to obtain a response about an order of magnitude higher than the response expected by the absorption methods described by other known researchers in the field. By using these techniques, blood glucose concentration can be non-invasively measured with a degree of accuracy and economy previously unattained.

DETAILED DESCRIPTION OF THE PREFERRED EMBODIMENTS

Figure 1:
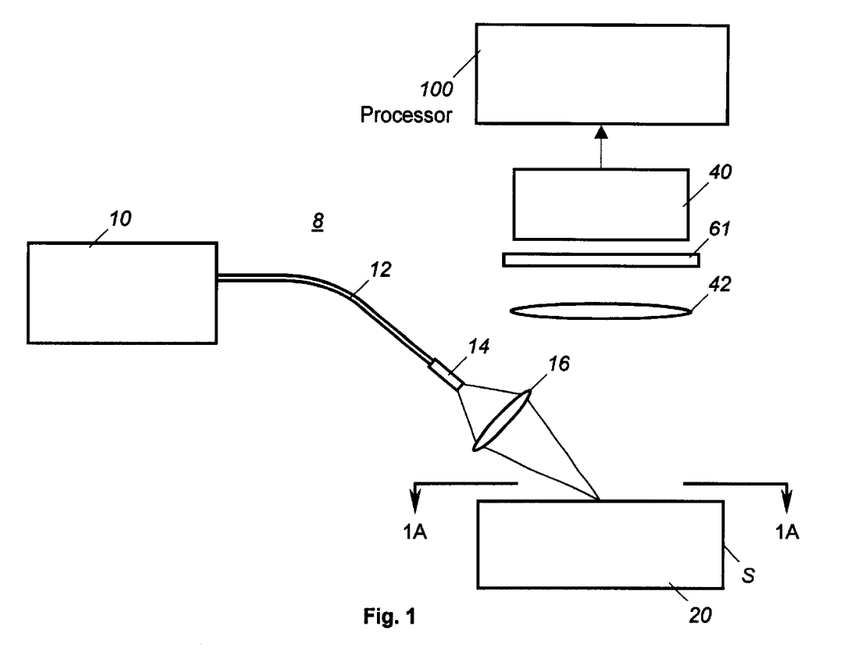
FIG. 1 is a schematic side elevational view of a preferred form of the present invention employing a line illumination on the surface of a subject.
Figure 1A:
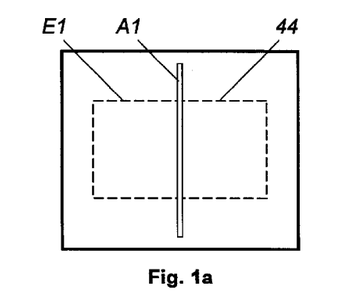
FIG. 1A is a top plan view of the surface of the subject taken along line a 1A—1A of FIG. 1.

Referring to FIGS. 1 and 1A, a preferred form of illuminator 8 for use in the preferred embodiment basically comprises a source of electromagnetic radiation 10, a fiber cable 12, and a line illuminator 14. One suitable line illuminator is manufactured by Fostec. The radiation emitted from line illuminator 14 is projected onto a surface 20 of a subject being studied S by a cylindrical lens 16. Alternatively, the line illuminator can be placed in contact or near the surface 20. Light source 10 may comprise a quartz halogen lamp equipped with a band-pass optical filter for selecting a suitable range of wavelength. Alternatively, a light emitting diode (LED) or a diode laser with suitable wavelength outputs can be used. The wavelength should be in the range from 400 nm to about 1600 nm. Lens 16 projects onto surface 20 a radiation pattern comprising a geometric element generated by moving a point in a path, either straight or curved to form a line, ring, semi-circle or other shape. For example, the geometric element comprising a line A1 on surface 20 may be defined by moving a point along a straight path to form a line. Of course, radiation from source 10 does not move along a path or surface 20 to illuminate the line A1. The width of the line, ring, semi-circle or other suitable shapes should be narrow, less than 1 mm, preferably less than 0.3 mm. A preferred line illuminator A1 has a length of about 50 millimeters and a width of 0.25 millimeters.

The radiation projected onto surface 20 diffuses into subject S and emits a part of the radiation from illuminated area A1, such area E1. At least a part of the radiation emitted from area E1 is detected by a CCD camera 40 through a lens 42, a linear variable neutral density (ND) filter 61 and a field of view 44. One suitable CCD camera is manufactured by Roper Scientific that is responsive to radiation in the 300–1100 nanometer wavelength range. The linear variable ND filter 61 is used to enhance the dynamic range of the CCD camera 40 in order to expand the dynamic range of the detection system: A suitable linear variable ND filter having graded optical density (OD) varying from 0 to 4 is manufactured by Reynard Corporation. The filter 61 may be mounted close to the CCD array detectors to minimize any stray light that may pass the filter. Field of view 44 is perpendicular to the line illumination A1. In addition, field of view 44 passes through about the middle half of the line illumination A1.

The image captured by CCD camera 40 can be digitized and processed by a processor 100. Multiple repeated images may be captured and averaged to improve the signal to noise ratio. It was found that the spatial reflectances (away from line A1) are nearly identical within about the middle half of the illumination line A1, provided that the length of the line A1 is twice as long as the maximum distance to be measured. Hence these profiles may be averaged to improve the signal to noise ratio. It may also be desirable to perform pixel-to-pixel ratioing against a reference profile, before averaging the profiles. The reference profile could be a profile under a normal glucose condition. Such a pixel-to-pixel ratioing and averaging approach could minimize the effects of non-uniformly within the line illumination A1, as well as minimize the effects of heterogeneity of the tissue structure as discussed below.

Local skin variation is of concern. Skin tissue is composed of various compositions of fat and protein, as well as veins, arteries, and bones. Such heterogeneous structure can contribute to local variation in the light absorption and scattering. Line illumination, as well as of other geometrical arrangements, is capable of averaging over a large skin area of the subject S. These illumination arrangements may indeed be used to reduce any local variation substantially, and thus improve reproducibility and reliability of the measurements.

Figure 2:
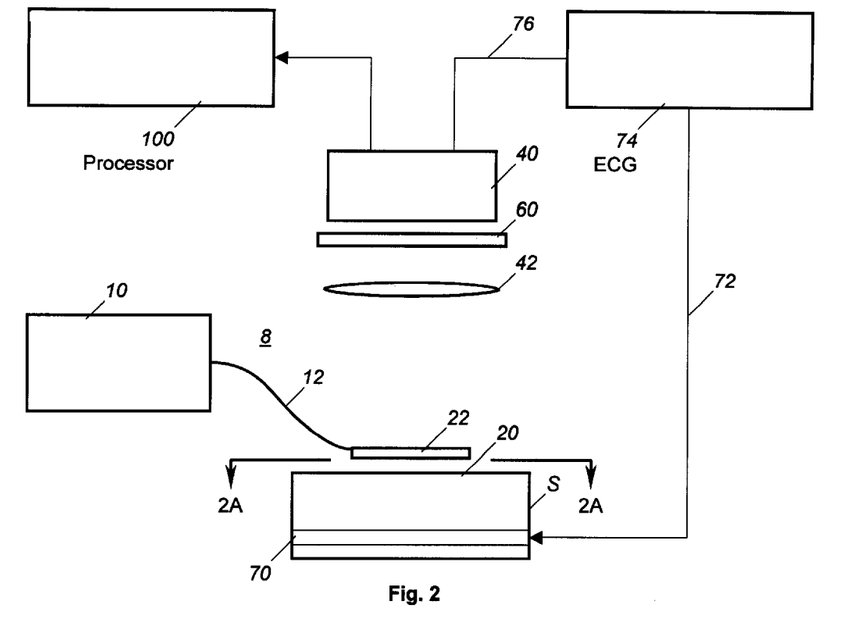
FIG. 2 is a schematic side elevational view of a preferred form of the invention employing a ring illumination on the surface of a subject and employing a CCD camera synchronized with the heart of a subject.
Figure 2A:
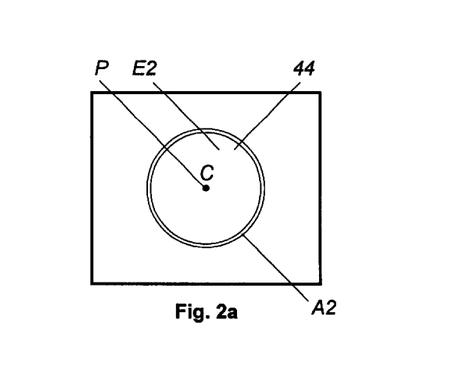
FIG. 2A is a top plan view of the surface of the subject taken along line 2A—2A of FIG. 2.

Referring to FIGS. 2 and 2A, much of the same apparatus shown in FIG. 1 is employed and bears like reference numbers. However, instead of employing a line illuminator 14, the embodiment of FIG. 2 employs a ring illuminator 22 which projects. onto surface 20 of subject S a ring illumination A2. The geometric element of A2 may be defined by moving a point in a path defining a closed curve, i.e., a circle. The radiation projected onto surface 20 by ring light 22 is diffused into subject S and is emitted from areas displaced from ring illumination A2, such as areas E2 encompassed by the ring.

The diameter of ring illumination A2 preferably has a diameter of 1.0 to 3.0 inches and more preferably the width of the ring should be less than 1 mm., preferably less than 0.3 mm. It has been discovered that 1.5 to 2.2 inches is an optimum diameter for non-invasive blood glucose detection.

Figure 3:
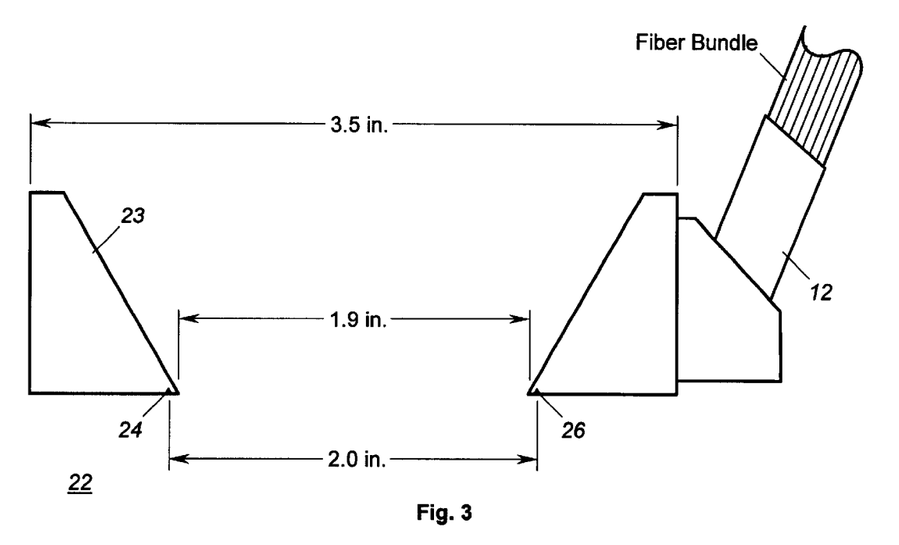
FIG. 3 is a cross-sectional view of a preferred form of ring light shown in FIG. 2.

FIG. 3 illustrates the example of a preferred form of a 2-inch diameter ring illuminator 22 which is manufactured by Forstec. As shown in FIG. 3, ring illuminator 22 has a center hole of 1.9 inch diameter through which a CCD camera can view. It is preferable that gap 26 between the fiber optic ring light 24 and the center edge of the center hole should be small to allow for measurements of the reflectance as close to the illumination site as possible. In addition, the ring illuminator 22 has a 30 degree taper back 23 to allow for a better field of view for camera 40 to the whole of area E2. The ring illuminator should be anodized except near the fiber optic ring 24 to minimize any stray scattered light. A radial variable ND filter 60, which is attached below the CCD array detector, is to enhance the dynamic range of the CCD camera 40. The ND filter 60 is radially symmetric: OD is low at the center P and gradually increases toward the edge. A suitable radial variable filter with OD of about 0 at the center and 4.0 near the edge, is manufactured by Reynard Corporation.

According to the FIG. 2 embodiment, processor 100 analyzes the detection signals generated by CCD camera 40 resulting from the field of view 44 receiving radiation from center point P to the edge of the area E2.

Referring to FIG. 2, the measured reflectances at all pixel locations within the area E2 are converted to a radial profile based on a coordination transformation with respect to the center point P. All the pixels that are within a same range of radial distance, as an example of one pixel size, may be averaged by the processor 100. It may be desirable to perform pixel-to-pixel ratioing to a reference profile before averaging over different azimuthal angles. The reference profiles could be obtained under a normal glucose condition. The averaging process could improve the signal to noise ratio, and also reduce any local variation caused by heterogeneous scattering structure in tissue.

Referring to FIGS. 1–2, and 1A–2A, illuminator 8 is used to illuminate the skin of a body part, including forearm; palm, abdomen, or thigh of a subject S being studied. Illuminator 8 may be placed directly in contact with the skin, or alternatively, illuminate the skin remotely by use of a lens or a reflector, as shown in FIG. 1.

As shown in FIG. 2, camera 40 may be triggered in synchronism with heartbeats of subject S which are detected by conventional electrocardiogram electrodes 70 which transmit electrical signals generated by the heart of subject S to a conventional electrocardiogram machine 74 that provides triggering signals to CCD camera 40 over a bus 76.

As a result, CCD camera 40 is triggered to receive data in response to systole of a heart within subject S. This synching arrangement is used to reduce a temporal variation in glucose concentration associated with blood flow changes.

Referring to FIGS. 1–2, processor 100 may comprise any conventional processor, such as a microprocessor or digital signal processor. Processor 100 is used to determine the glucose levels of subject S by comparing the measured diffuse reflectance profiles transmitted as detector signals by CCD camera 40 with pre-calibrated profiles.

Alternatively, the glucose levels of subject S can be determined from ratios of the diffuse reflectance profiles with respect to a reference one, such as one obtained under a normal glucose level condition, and by comparison with pre-calibrated ratioed data.

Still referring to FIGS. 2 and 3, it has been unexpectedly found that a line or ring illumination can be used to improve detection sensitivity by a factor as high as an order of magnitude as compared to point illumination. In addition, a line or ring illuminations permits measurements of the reflectance at a distance much farther away from the illumination site than point illumination. Since the effective average radiation penetration is deeper into the skin at a farther distance, it permits interaction of the photons at a depth where the glucose is expected to be more abundant. The interaction with the rich glucose region further results in improved detection sensitivity as compared to point illumination.

FIGS. 1–2 and FIGS. 1A–2A illustrate two of the preferred illumination arrangements, namely line illumination and ring illumination. Variations from these two arrangements may include a semi-circular ring, rectangular and other suitable geometric arrangements that can achieve high glucose measurement sensitivity and in the mean time reduce local variation caused by tissue heterogeneity. In addition, other types of imagers, including CMOS and line scanner cameras may be used in replacing a CCD camera to achieve compactness of the device and also to reduce the cost. Alternatively, several photodiodes may be used to measure the spatial reflectance profiles, with the advantages of independent gain setting among different photodiodes to measure a large variation among reflectance intensities.

EXAMPLE 1

Figure 4:
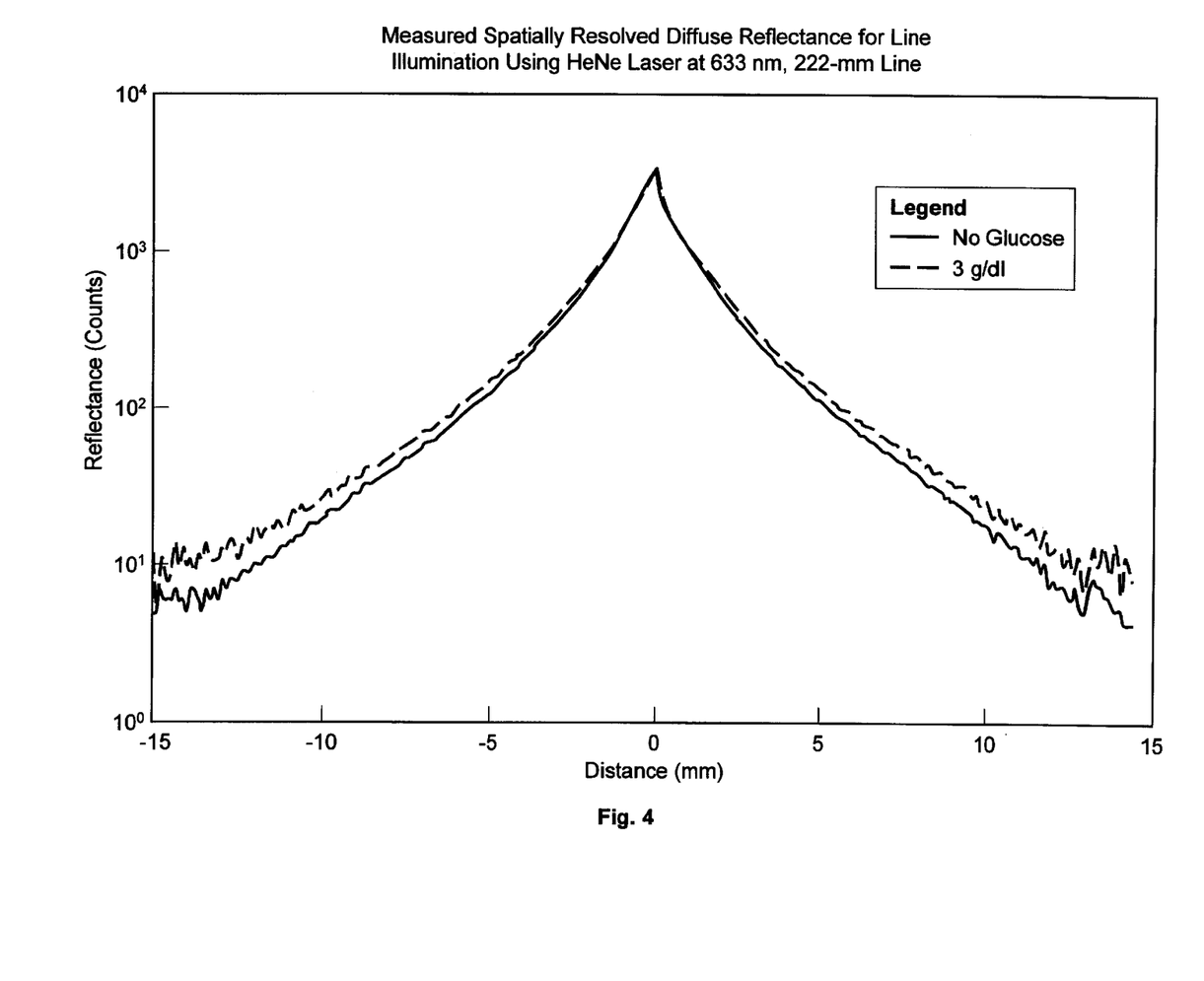
FIG. 4 is a graph illustrating spatially resolved diffuse reflectance intensity in counts versus distance for a line illumination using a halogen lamp and a line illuminator which is 22 millimeters in length employing 1% Intralipid solution as a phantom tissue.
Figure 5:
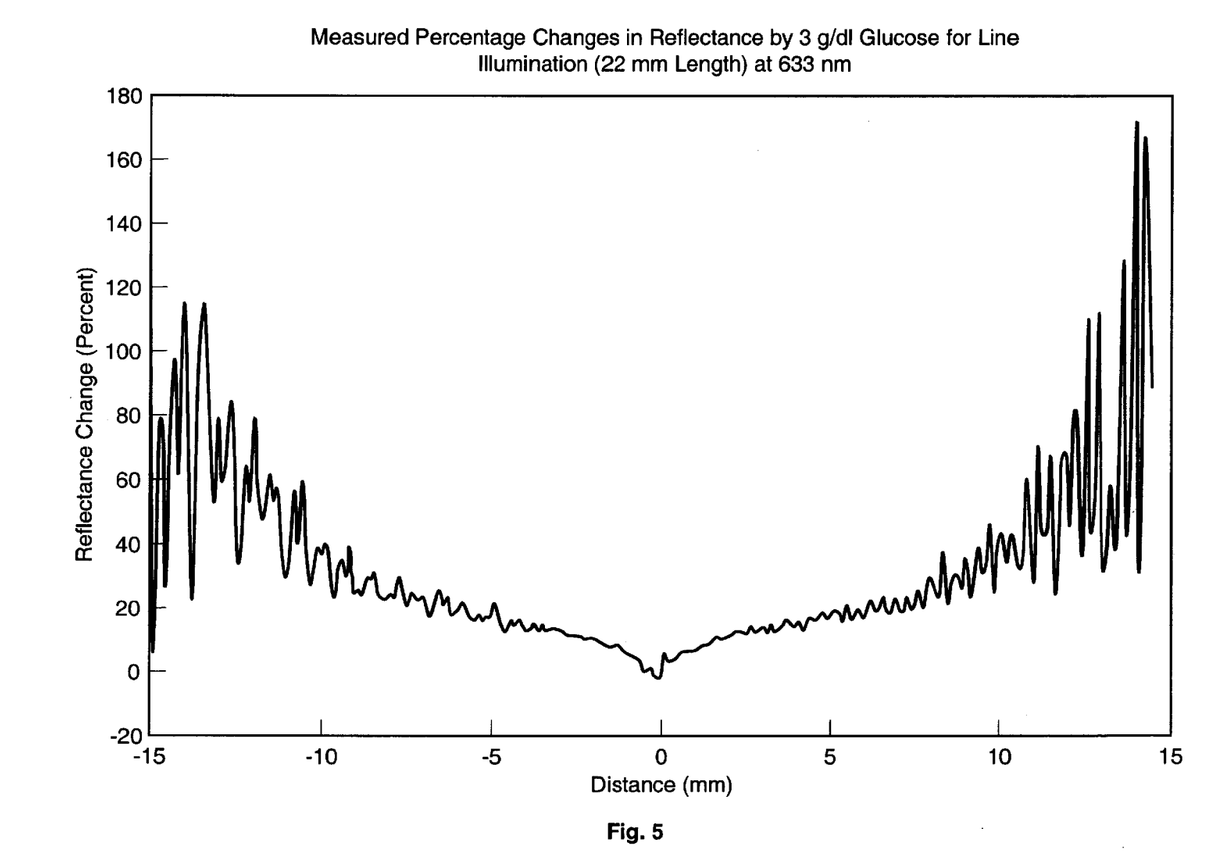
FIG. 5 is a graph illustrating percentage changes in reflectance by three grams per deciliter glucose concentration versus distance in millimeters for a line illumination using a line illuminator 22 millimeters in length.

An experiment using a line illumination arrangement similar to the arrangement shown in FIGS. 1 and 1A was performed. A HeNe laser beam at 633 nm was expanded by a beam expander and then focused into a line, such as line A1, by use of a cylindrical lens like lens 16. The length of the line was approximately 22 mm and the width of the line was approximately 0.3 mm. The laser beam was projected at a 50-degree inclination angle normal to the surface 20 of a 1% Intralipid solution (supplied by VWR). The Intralipid solution with various glucose concentrations was used as a phantom tissue to simulate the scattering and absorption events in human tissue. A CCD camera 40 (assembled by TRW, Inc.) was used to measure the spatial profile at the midpoint and normal to the illumination line A1. FIG. 4 compares the results of the reflectance profiles for the Intralipid solution with 3000-mg/dl glucose to the Intralipid solution without glucose. FIG. 5 shows that the fractional changes are small near the illumination site and become larger at longer distances away from the illumination site.

A separate experiment using a point illumination via a tightly focused HeNe laser also was conducted for comparison. The reflectance intensity resulting from the line illumination dropped much more slowly than the reflectance intensity resulting from the point illumination. The attainable distance from line A1 before the signal was overwhelmed by noise appeared to be much longer for line illumination than for point illumination. In addition, the attainable fractional changes before the signal was overwhelmed by noise were significantly higher for line illumination compared to point illumination.

EXAMPLE 2

An experiment using a ring illumination similar to the illuminator shown in FIGS. 2 and 2A was performed. A light emitting diode (LED) at 880 nm was used as illumination source 10. The light output from the LED was launched from one end of fiber bundle 12 that led to a 2-inch-diameter ring light (manufactured by Schott-Fostec LLC) illuminator 22. The width of the ring light was approximately 0.3 mm. The ring light was placed approximately 0.1 mm above surface 20 of an Intralipid solution. A CCD camera 40 (manufactured was Roper Scientific) was used to image the reflectance profiles near the center of the ring light through an annual-cone light baffle. The light baffle was used to minimize stray light. The images of the CCD camera (512 by 512 pixels) were captured and digitized by a frame grabber.

Individual pixels were corrected for dark background and were calibrated by a white light field. Fractional changes in reflectance were calculated firstly by applying a pixel-to-pixel ratioing process comparing reflectance in the presence of glucose to reflectance in the absence of glucose. A radial profile for the fractional changes in reflectance then was obtained by averaging over the entire range of azimuthal angles of interest. It was found that such a pixel-to-pixel ratioing can be used to correct any distortion caused by any non-uniformity in the illumination intensity along ring light illumination A2. This is because any non-uniformity tends to distort the image of the reflectance intensity profile from that of a radially symmetrical profile, whereas the pixel-to-pixel rationing process restores the profile in the fractional changes to a nearly radially symmetrical profile.

Figure 6:
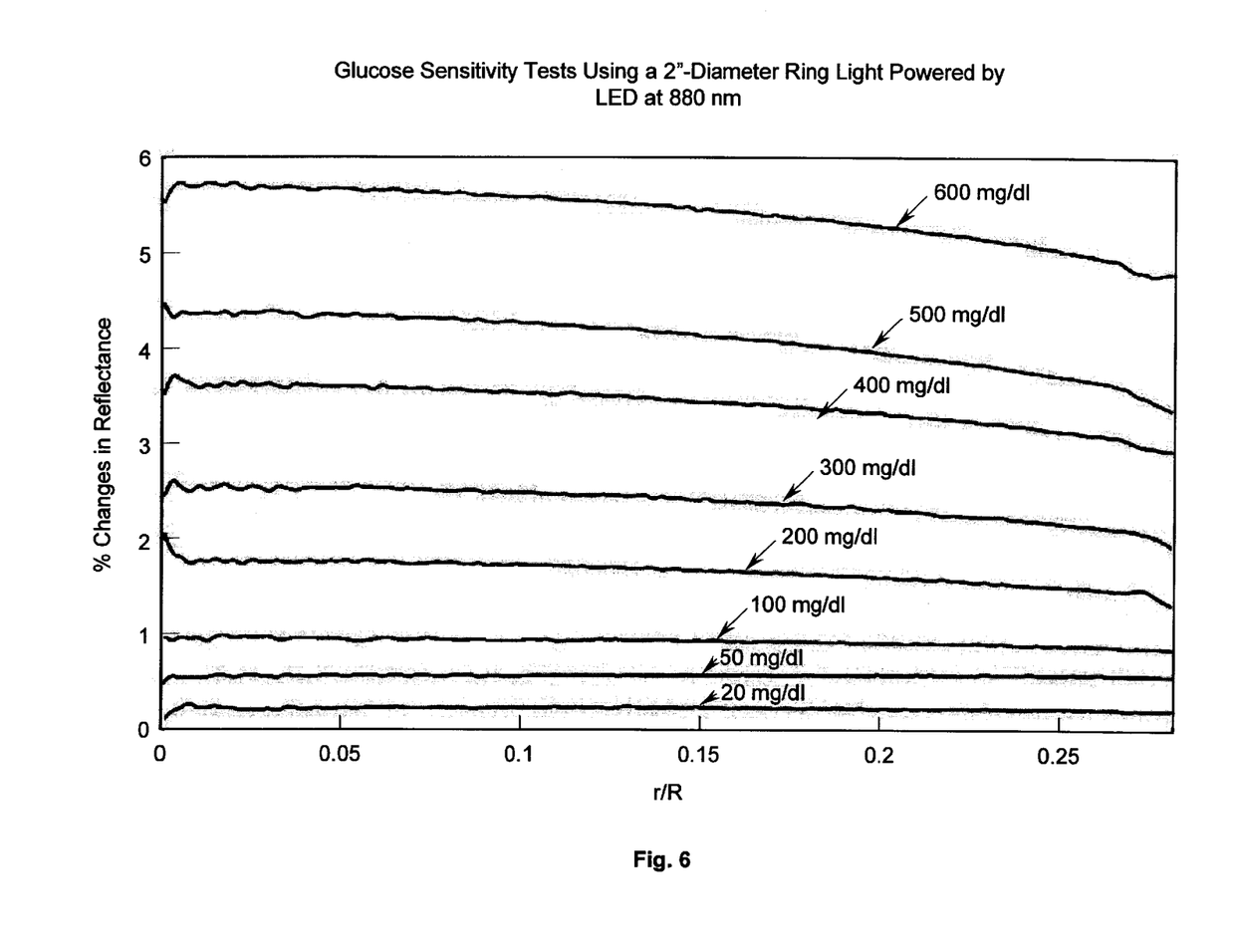
FIG. 6 is a graph illustrating percentage changes in reflectance by various milligrams per deciliter glucose concentrations versus distance from the center point divided by the radius of a 2 inch diameter ring illuminator powered by an LED at 880 nanometers.

FIG. 6 shows the results of the fractional changes in reflectance as functions of r/R for Intralipid solutions containing several glucose concentrations from 20 to 600 mg/dl to that in the absence of glucose. Here r is the radial distance from the center P of the ring illumination A2 and R is the radius of the ring illumination A2. Typically about 8 repeated tests were conducted for each glucose solution. Each curve, shown in FIG. 6 results from an average of the 8 tests. The standard deviation was found to be about 20 mg/dl among the 8 tests. This result suggests that the present invention has sufficient sensitivity for noninvasive monitoring of glucose level in skin tissue.

Those skilled in the art will recognize that only the preferred embodiments of the invention have been described in this specification. These embodiments may be modified and altered without departing from the true spirit and scope of the invention as defined in the accompanying claims.

What is claimed is:

1. Apparatus for noninvasive measurement of glucose concentration in a biological matrix of a subject comprising in combination:

a source of electromagnetic radiation generating an illuminated first portion of surface of the subject, said first portion comprising a geometric element defined by moving a point in a path, said illuminated first portion resulting in a part of said radiation being emitted from said surface in a second portion of the surface displaced from the first portion, said first portion comprising one of a straight line and a closed curve defining a center point;

a detector or detectors defining a field of view and responsive to said radiation emitted from at least a part of the second portion within the field of view to generate detection signals, said field of view defining one of a rectangle perpendicular to said straight line and a portion of the area within the inside of said closed curve passing through the center point; and a processor analyzing said detection signals to measure blood glucose of the subject.

2. Apparatus, as claimed in claim 1, wherein the source comprises radiation having wavelengths in the range of 400 to 1600 nanometers.

3. Apparatus, as claimed in claim 1, wherein the detector comprises a camera, a CCD camera, a CMOS or near-infrared imager, or photodiode detectors.

4. Apparatus, as claimed in claim 3, wherein the subject comprises a heart and further comprising a trigger for said detector responsive to signals generated by said heart.

5. Apparatus, as claimed in claim 3, wherein the detector further comprises a graded neutral density filter.

6. Apparatus, as claimed in claim 1, wherein the processor compares said detection signals to a reflectance profile based on calibration measurements from conventional blood glucose measurements of said subject.

7. Apparatus, as claimed in claim 1, wherein the geometric element defines a straight line, with the width of the line less than 0.3 mm.

8. Apparatus, as claimed in claim 1, wherein the processor compares said detection signals to one or more reflectance profiles.

9. Apparatus, as claimed in claim 1, wherein the rectangle passes through the middle half of the straight line.

10. Apparatus, as claimed in claim 1, wherein the processor analyzes the detection signals resulting from the portions of the field of view receiving radiation displaced 0 to 30 mm, from said straight line.

11. Apparatus, as claimed in claim 1, wherein the processor analyzes the detection signals resulting from the portions of the field of view receiving radiation from the portion of the area inside said curve.

12. A noninvasive method of measuring blood glucose of a subject comprising in combination:

illuminating with electromagnetic radiation a first portion of a surface of the subject comprising a geometric element defined by moving a point in a path, said illuminated first portion resulting in a part of said radiation being emitted from a second portion of said surface displaced from the first portion, said first portion comprising one of a straight line and a closed curve defining a center point;

generating detection signals responsive to said radiation emitted from at least a part of the second portion within a field of view, said field of view defining one of a rectangle perpendicular to said straight line and a portion of the area within the inside of said closed curve passing through the center point; and analyzing said detection signals to measure the blood glucose of the subject.

13. A method, as claimed in claim 12, wherein said illuminating comprises illuminating with radiation having wavelengths in the range of 400 to 1600 nanometers.

14. A method, as claimed in claim 12, wherein said generating comprises digital imaging.

15. A method, as claimed in claim 14, and further comprising triggering said generating responsive to signals generated by a heart beat oF said subject.

16. A method, as claimed in claim 15, wherein said generating further comprises graded neutral density filtering.

17. A method, as claimed in claim 12, wherein said straight line has a width of less than 1 mm.

18. A method, as claimed in claim 12, wherein the rectangle passes through the middle half of said straight line.

19. A method, as claimed in claim 12, wherein said analyzing comprises analyzing the detection signals resulting from the portions of the field of view receiving radiation displaced 0 to 15 mm from the straight line.

20. A method, as claimed in claim 12, wherein the analyzing comprises comparing said detection signals to one or more reflectance profiles.

21. A method, as claimed in claim 12, wherein the analyzing comprises comparing said detection signals to a reflectance profile based on calibration measurements from conventional blood glucose measurements of said subject.

* * * * *